US012064266B2

(12) United States Patent
Pierart et al.

(10) Patent No.: US 12,064,266 B2
(45) Date of Patent: Aug. 20, 2024

(54) MICRONEEDLE INDENTATION MANAGEMENT

(71) Applicant: PKvitality, Paris (FR)

(72) Inventors: Luc Pierart, Villejuif (FR); Anh-Minh Lê, Neuilly-Sur-Seine (FR)

(73) Assignee: PKvitality, Paris (FR)

( * ) Notice: Subject to any disclaimer, the term of this patent is extended or adjusted under 35 U.S.C. 154(b) by 855 days.

(21) Appl. No.: 17/265,438

(22) PCT Filed: Aug. 2, 2019

(86) PCT No.: PCT/EP2019/070947
§ 371 (c)(1),
(2) Date: Feb. 2, 2021

(87) PCT Pub. No.: WO2020/025822
PCT Pub. Date: Feb. 6, 2020

(65) Prior Publication Data
US 2021/0353229 A1 Nov. 18, 2021

(30) Foreign Application Priority Data
Aug. 3, 2018 (FR) ...................................... 1857291

(51) Int. Cl.
*A61B 5/00* (2006.01)
*A61B 5/145* (2006.01)
*A61B 5/15* (2006.01)

(52) U.S. Cl.
CPC .......... *A61B 5/685* (2013.01); *A61B 5/14546* (2013.01); *A61B 5/150022* (2013.01);
(Continued)

(58) Field of Classification Search
CPC ............... A61B 5/685; A61B 5/14546; A61B 5/150022; A61B 5/150969;
(Continued)

(56) References Cited

U.S. PATENT DOCUMENTS

2003/0083645 A1\* 5/2003 Angel ............... A61M 5/14248
604/890.1
2010/0249560 A1\* 9/2010 Levinson ............... A61B 5/411
600/364
(Continued)

FOREIGN PATENT DOCUMENTS

WO    2014/120114 A1    8/2014

OTHER PUBLICATIONS

International Search Report dated Oct. 8, 2019 in International Application No. PCT/EP2019/070947.
French Search Report Dated May 31, 2019 in FR Application No. 1857291.
Written Opinion of the International Searching Authority Dated Oct. 8, 2019 in International Application No. PCT/EP2019/070947.

*Primary Examiner* — Eric F Winakur
*Assistant Examiner* — Abid A Mustansir
(74) *Attorney, Agent, or Firm* — Sughrue Mion, PLLC

(57) ABSTRACT

A sensor (220) for a body monitoring system (1), having analyte-measuring microneedles (210) that extend parallel to a main direction (Z) from a substrate (242) and define a working plane (Pt), wherein the sensor (220) has at least one conductivity electrode (600) with a metallic track (602), the end of the metallic track extending along the main direction (Z) to a position strictly between the substrate (242) and the working plane (Pt).

16 Claims, 3 Drawing Sheets

Figure 1:
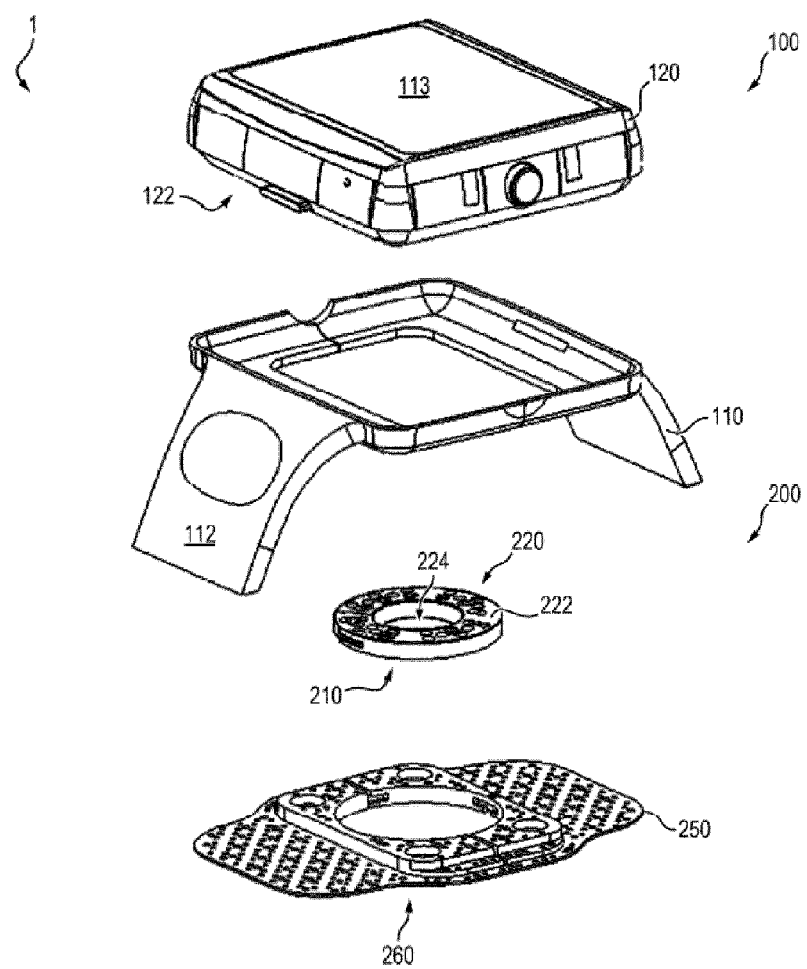

(52) U.S. Cl.
CPC .. *A61B 5/150969* (2013.01); *A61B 5/150984* (2013.01); *A61B 5/6824* (2013.01); *A61B 5/6831* (2013.01); *A61B 5/6833* (2013.01); *A61B 5/6839* (2013.01); *A61B 5/6886* (2013.01); *A61B 2560/0412* (2013.01); *A61B 2562/0295* (2013.01)

(58) Field of Classification Search
CPC ............ A61B 5/150984; A61B 5/6824; A61B 5/6831; A61B 5/6833; A61B 5/6839; A61B 5/6886; A61B 2560/0412; A61B 2562/0295; A61B 5/157; A61B 2560/0468; A61B 5/681; A61B 5/0531; A61B 5/14503; A61B 5/14514; A61B 5/053; A61B 5/068
See application file for complete search history.

(56) References Cited

U.S. PATENT DOCUMENTS

| | | | |
|---|---|---|---|
| 2011/0224515 A1* | 9/2011 | Mir .................... | A61B 5/15151 600/317 |
| 2014/0275897 A1 | 9/2014 | Pushpala et al. | |
| 2015/0208984 A1 | 7/2015 | Huang | |
| 2017/0347925 A1 | 12/2017 | Wang et al. | |
| 2019/0076075 A1* | 3/2019 | Miller .............. | A61B 5/150022 |
| 2019/0357830 A1* | 11/2019 | Visweswara ..... | A61B 5/150862 |

* cited by examiner

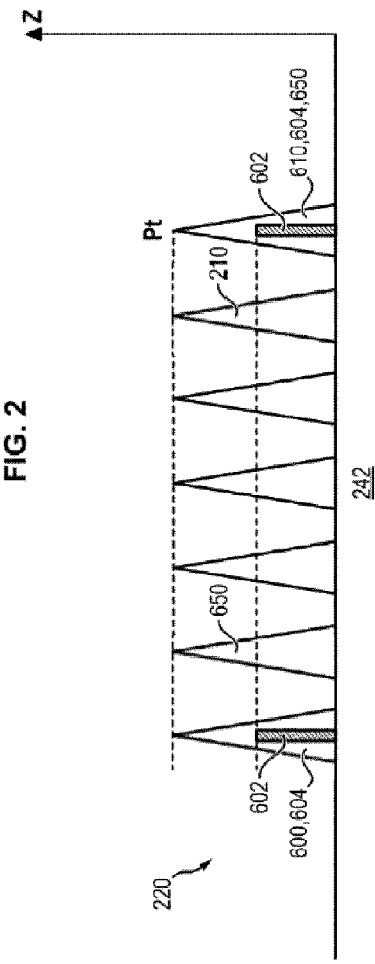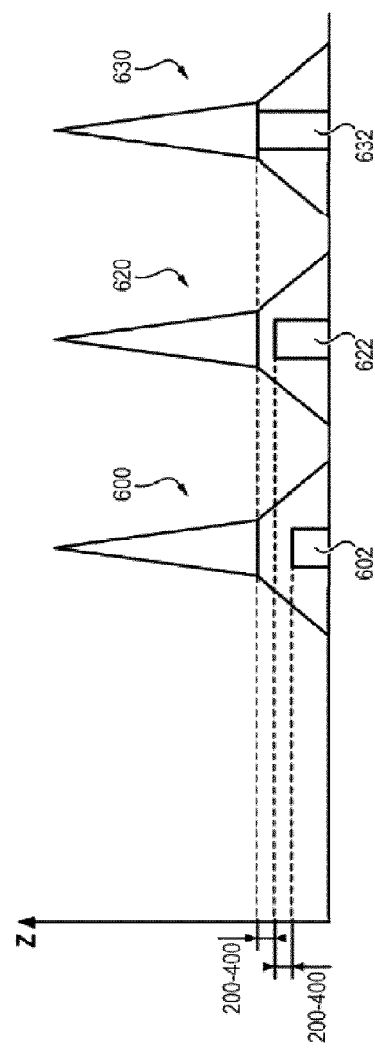

MICRONEEDLE INDENTATION MANAGEMENT

CROSS REFERENCE TO RELATED APPLICATIONS

This application is a National Stage of International Application No. PCT/EP2019/070947 filed Aug. 2, 2019, claiming priority based on French Patent Application No. 1857291 filed Aug. 3, 2018.

GENERAL TECHNICAL FIELD

The present invention relates to a body monitoring system via body, typically interstitial, fluid analysis using microneedles.

More specifically, the present invention concerns the management of the holding of the microneedles in the skin.

STATE OF THE ART

Some pathologies such as diabetes require daily monitoring of biochemical parameters of the human body, i.e. concentrations of some compounds (glycemia in the example of glucose).

To this end, it is common to prick a point of the skin so as to bead up a drop of blood, and to analyze this drop either reactively (for example with a strip) or electronically (for example by at least one analytical sensor), so as to estimate the target parameter(s).

Much less invasive advanced systems are known today, which simply analyze the interstitial fluid, that is to say, the fluid that fills the space between blood capillaries and cells. It has indeed an ionic composition close to that of blood plasma.

These advanced systems thus allow monitoring the desired biochemical parameters transcutaneously that is to say without the need to evenly pierce the skin and take samples.

Devices with microneedles are known, which have the advantage of being less invasive than conventional needles. However, it is important that these microneedles remain in place.

There are for that purpose indwelling devices where microneedles are held on the skin with an adhesive tape. However, it is desirable to be able to carry out a continuous or quasi-continuous control, which requires autonomous devices. The GlucoWatch device, which used iontophoresis (and not needles) can be cited.

The device is also known from document WO2018104647, which has a casing comprising a removable capsule, the capsule accommodating microneedles configured to sample interstitial fluid. The casing, for its part, accommodates most part of the electronics.

However, when such a device includes microneedles, there may be difficulties related to the insertion of the microneedles into the skin.

The invention aims at overcoming these difficulties.

PRESENTATION OF THE INVENTION

In order to address difficulties mentioned above, the invention proposes a sensor for a body monitoring system, comprising analyte measurement microneedles configured to be inserted into the skin to sample and/or analyze a body fluid from the wearer of the sensor when the latter is positioned on the limb, wherein the analyte measurement microneedles extend parallel to a main direction from a substrate and define a working plane corresponding to the plane passing through the tip of the analyte measurement microneedles, the analyte measurement microneedles each comprising on their surface a biochemical material able to react with the analyte, characterized in that the sensor comprises at least one microneedle separate from the analyte measurement microneedle, on which is mounted a conductivity electrode configured to measure the level of penetration of the analyte measurement microneedle in the epidermis, the conductivity measurement electrode comprising a metal track, the end of the metal track extending along the main direction up to a position comprised strictly between the substrate and the working plane, the two being therefore excluded, the sensor comprising another conductivity electrode, operating as a reference conductivity electrode, said reference electrode comprising a metal track whose end can reach the working plane.

The working plane is advantageously defined by the tip of the analyte measurement microneedles or the plane of the sampling orifices (in the case of microneedles which sample fluid).

In one embodiment, the metal track of each conductivity electrode (therefore including the reference electrode) has a length smaller than that of the biochemical measurement microneedles, the two tracks having preferably the same length.

In one embodiment, each conductivity electrode is mounted on a conductivity microneedle, of a length equal to that of the analyte measurement microneedles.

In one embodiment, the conductivity electrode is mounted on a conductivity microneedle which is only partially coated with the metal track.

In one embodiment, the conductivity microneedle is integrally covered with metal, preferably for the reference electrode.

In one embodiment, the metal track covers an entire portion of the microneedle, in order to increase the metal surface for a given position.

In one embodiment, the sensor comprises, distributed over one or several conductivity microneedle(s), a plurality of conductivity electrodes each comprising a metal track extending along the main direction up to at least two different positions, the positions being strictly comprised between the substrate and the working plane.

In one embodiment, the metal tracks are all placed on the same microneedle.

In one embodiment, the microneedle has a frustoconical pyramidal shape comprising at least two faces and in which the metal tracks are distributed over several faces, preferably one track per face.

In one embodiment, the metal tracks are placed on different microneedles.

In one embodiment, the two positions are spaced apart by 200 μm to 400 μm along the main direction.

In one embodiment, the end of the track of the reference conductivity electrode is at the same position as the end of the metal track of the longest conductivity electrode.

In one embodiment, the plurality of metal tracks comprises three metal tracks.

In one embodiment, the arrangement of the conductivity electrodes is made such that the analyte measurement microneedles are located between two conductivity microneedles.

The invention also proposes a body monitoring system, intended to be attached to a limb, comprising:
a capsule comprising a sensor as described previously,
a casing, able to be coupled with the capsule, inside which there is a battery and a processor, the processor being configured to process data obtained using the sample or the measurement taken by the microneedles, the processor and the battery being configured to manage the conductivity measurements using the electrodes.

The system may further comprise:
a strap or a bracelet, configured to hold the casing in place on a limb,
a patch, the capsule being removably attachable to the patch and the patch being removably attachable to the casing, the patch having an adhesive role.

Another aspect of the invention is a method for measuring the level of penetration in the epidermis of the analyte measurement microneedles of a sensor according to the invention, comprising at least one step of measuring the conductivity between a conductivity electrode and the reference conductivity electrode.

PRESENTATION OF THE FIGURES

Other characteristics and advantages of the present invention will become apparent upon reading the following description of a preferred embodiment. This description will be given with reference to the appended drawings in which:

FIG. 1 illustrates an exploded view of a bracelet, a casing, a capsule and a patch as usable in the framework of the invention, FIG. 2 illustrates a sensor according to one embodiment of the invention, FIGS. 3 to 6 illustrate different variants of a sensor according to another embodiment of the invention.

DETAILED DESCRIPTION

Sensor

In relation to FIGS. 1 to 6, a sensor comprising analyte measurement microneedles 210 configured to be inserted into the skin in order in particular to sample and/or analyze a body fluid from an individual will be described. In the case of pierced microneedles forming a channel in each microneedle, a sample can be taken by fluidly connecting a system for pumping the interstitial fluid to the channel, or simply by capillarity. An analysis system can comprise microneedles each provided with an electrode or a set of electrodes, or be offset after the microneedles, so as to cause an electrochemical reaction adapted to detect an analyte in the interstitial fluid.

Particularly, the sensor is mounted on a capsule 220 (FIGS. 1 and 6) which removably cooperates with a casing 120 to form a body monitoring system 1 attachable to a limb (typically a wrist). This system will be described in more detail in the end of the description. Reference 220 will apply to both the sensor and the capsule.

The sensor 220 comprises a plurality of analyte measurement microneedles 210. These analyte measurement microneedles 210 are used to sample fluid or directly to measure a quantity relating to an analyte.

Figure 6:
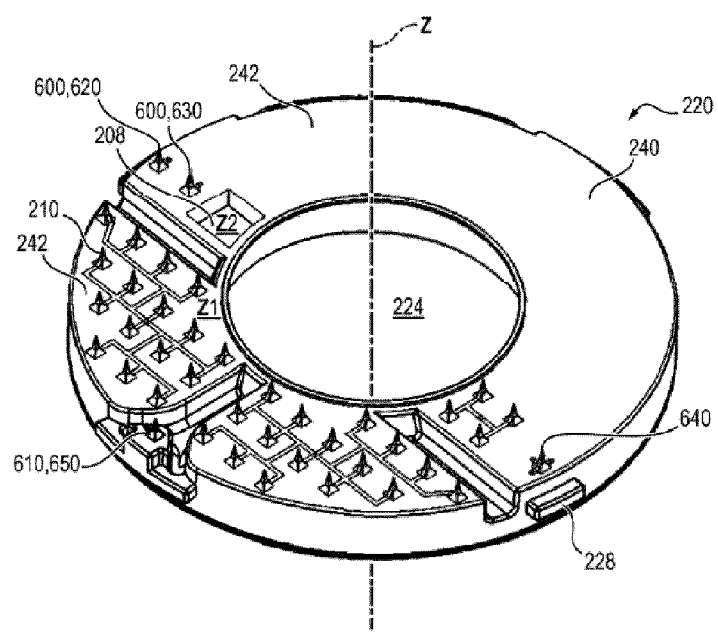

The measurement microneedles 210 advantageously consist of an array of measurement microneedles 210 in contact with the skin when the capsule 220 is placed on the body of a person (FIG. 6). The analyte measurement microneedles 210 can therefore be either hollow, to sample fluid, or full, to analyze the fluid directly. In the first case, typically, the analyte measurement microneedles 210 allow the extraction of interstitial fluid from the dermis painlessly without beading up blood, and send it to a sensor. In the second case, the analyte measurement microneedles 210 do not sample any fluid and integrate the sensor on their surface, in the form of a biochemical material able to react with the analyte desired be measured in the fluid.

Preferably, the array of analyte measurement microneedles 210 comprises between four and fifty, substantially pyramidal, microneedles with tips of a height comprised between 100 µm and 1,000 µm, preferably 0.3 mm and 0.8 mm. Each of these advantageous characteristics of the analyte measurement microneedles 210 can be taken separately or in combination with the other ones.

Each analyte measurement microneedle 210 extends from a substrate 242 along a main direction Z (orthogonally to the substrate which defines a contact face 222). These measurement microneedles 210 define a working plane Pt: this working plane Pt corresponds to the plane passing through the tip of these analyte measurement microneedles 210 or alternatively to the plane passing through the sampling orifices of the analyte measurement microneedles 210, which are generally located at the end or in the vicinity of the end.

With regard to analyte measurement microneedles 210, it is essential to know the level of penetration of the analyte measurement microneedles 210 in the epidermis.

In this respect, the sensor integrates at least one conductivity electrode 600 which is used to measure the conductivity of the medium in which it is located. The conductivity electrode 600, which extends from the substrate 242, comprises a metal track whose end extends, along the main direction Z, up to a position strictly comprised between the substrate 242 and the working plane Pt of the measurement microneedles 210. This means, in other words, that the conductivity electrode 600 measures the conductivity for fluid located between the tip of the measurement microneedles 210 and the outside of the skin.

Thanks to this conductivity electrode 600, it is possible to know whether the measurement microneedles 210 are sufficiently penetrating or not.

For example, the metal track 602 extends up to between 200 and 400 µm from the substrate 242 along the main direction Z.

A reference conductivity electrode 650, for its part, comprises a metal track whose end may extend, along the main direction Z, up to a position strictly comprised between the substrate 242 and the working plane Pt of the measurement microneedles 210. Alternatively, the end can extend up to the working plane Pt.

The conductivity measurement is therefore taken between the conductivity electrode and the reference conductivity electrode.

The arrangement of the conductivity electrodes 600, 650 is made such that the analyte measurement microneedles 210 are located between two conductivity microneedles 600, 650. In the case where several electrodes 600 work with a single reference conductivity electrode 650, their disposition is made to always have analyte measurement microneedles 210 in the center.

Electrode and Microneedle

The conductivity electrode 600 can be made in the form of a microneedle 604 comprising a metal track 602 extending up to the desired position. The metal track 602 can be made on a surface of the microneedle or it can be buried in the microneedle with only the end of the metal track 602 that protrudes. Consequently, the position of the electrode 600 on the microneedle 604 is not that of the end of the microneedle 604. In addition, the microneedle 604 is therefore only partially covered with metal.

The electrodes 600, 650 are electrically connected to an electrical connector so that they can then be powered on by means of a conductimetric module which uses a processor and a battery. These components will be described in more detail below.

The conductivity microneedle has advantageously the same length as the analyte measurement microneedles 210 (extending from substrate areas forming part of the same plane) in order to simplify the manufacturing methods.

The metal track may only partially cover a portion of the microneedle or cover the entire microneedle up to the desired height (to improve the contact surface with the outside—in particular for the conductivity electrodes of shorter length than the reference conductivity electrode).

First Embodiment

In one embodiment (FIG. 2), a second electrode 610, identical to the one described above (which is called first electrode 600 in this case) is provided. This second electrode 610 corresponds to a reference conductivity electrode 650 mentioned above. The conductivity measurement is therefore taken between these two electrodes 600, 610 whose electrodes are shorter than the microneedles 210. If a straight line passing through the end of these electrodes (the end of the metal tracks 602) is defined, it is parallel to the working plane Pt, but not coincident. Thus, a method for measuring the level of penetration of the analyte micro-needles 210 into the epidermis can be implemented by measuring the conductivity between the two conductivity electrodes 600 and 610.

The second conductivity electrode 610 is preferably mounted on a microneedle, in the same way as has been described for the first conductivity electrode 600.

Second Embodiment

In another embodiment (FIGS. 3 to 6), several conductivity electrodes 600, 620, 630 each comprising a metal track 602, 622, 632 which extends from the substrate at positions different from each other along the main direction Z. These positions are all strictly comprised between the working plane Pt and the substrate 242.

The conductivity measurement is taken between one of these conductivity electrodes 600, 620, 630 and the reference conductivity electrode 650. Thus, a method for measuring the level of penetration of the analyte microneedles 210 in the epidermis can be implemented by measuring the conductivity between the conductivity electrodes 600, 620 and 630.

These different conductivity electrodes 600, 620, 630 allow knowing more accurately the level of penetration of the microneedles 210. Indeed, with reference to FIGS. 3 and 4, if the conductivity electrode 600 (the shortest one) has a conductivity relating to an immersion, then the microneedles 210 are sufficiently penetrating. If, on the other hand, only the conductivity electrodes 620, 630 (the longest ones) have a conductivity relating to an immersion, then there is a risk that the penetration is not sufficient. If only the conductivity electrode 630 has a conductivity relating to an immersion, then there is a risk that the analyte measurement microneedles are not sufficiently penetrating.

The principle is generalizable to more electrodes.

Preferably, the reference conductivity electrode 650 is similar to the conductivity electrode 630—therefore the deepest one.

The height difference along the main direction Z between two metal tracks 602, 622, 632 of two conductivity electrodes 600, 620, 630 is typically comprised between 50 μm and 400 μm, preferably between 50 and 150 μm. For example, if there are three electrodes, there can be a deviation of 200 μm between the first and the second one and 200 μm between the second and the third one. The track 602 (the shortest one) is typically located between 50 and 400 μm from the substrate 242 along the main direction Z.

The conductivity electrodes 600, 620, 630 can be mounted on separate microneedles, as illustrated in FIG. 3.

Figure 4:
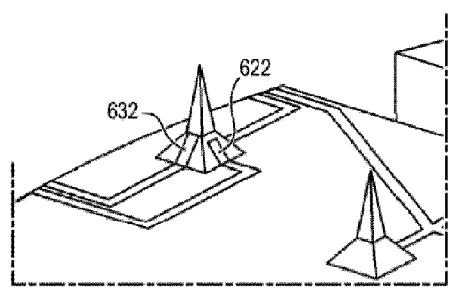
Figure 5:
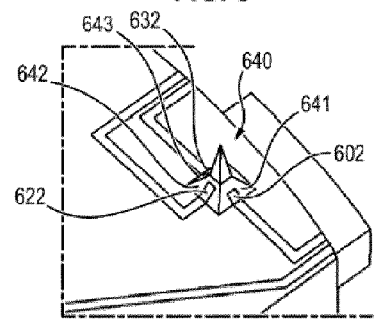

Alternatively, the electrodes 600, 620, 630 can be mounted on a single microneedle 640 (FIGS. 4 and 5). In one variant, the tracks 602, 622, 632 are present on the same face of the microneedle 640. In a preferred variant, a microneedle 640 is chosen with a frustoconical (for example pyramidal) portion having at least three (or even four) lateral faces 641, 642, 643: the electrodes are thus disposed on different faces of the pyramidal frustoconical shape.

During each conductivity measurement, each conductivity electrode 630, 640 therefore behaves like an electrode 600 as presented in the general formulation of the invention, compared to the reference conductivity electrode 650.

These two alternatives can be both mounted on the same sensor, in order to have some redundancy. FIG. 6 illustrates it.

General Architecture

With reference to FIG. 1, which represents a general diagram, the present invention concerns an electronic body monitoring system 1.

By "body monitoring" is meant the verification of biochemical constants of a person wearing the system 1, typically the concentration of a protein, a hormone, a marker, oxygen, nutrients, etc., in the interstitial fluid of the person. The example of glycemia can be cited. Those skilled in the art will be able, if necessary, to monitor other physical body quantities such as lactate, hydration etc.

The description will be illustrated with interstitial fluid but applies to the other body fluids such as blood.

The system 1 is said to be autonomous because it does not require the use of additional equipment.

The system 1 is formed of two modules 100, 200 (FIG. 1) interconnected by a separable link 300 which is reusable.

The first module 100 comprises in particular means for attaching and tightening 110 the system 1 to a limb (called strap 112 or bracelet) and the second module 200 comprises a capsule 220 that integrates the sensor, as mentioned above.

The two modules 100 and 200 each have a coupling face 122, 222, of complementary shape, which allows placing the second module 200 in a location for accommodating the first module 100.

Finally, the first module 100 and the second module 200 are configured to be coupled by the separable link 300.

As illustrated in FIG. 1, the first module 100 further comprises a casing 120 in which are disposed data processing means (particularly a processor or a microcontroller) configured to process measurements acquired by the sensor, and where appropriate, data storage means (in particular a memory, particularly of the flash type, and/or the memory of the microcontroller) allowing for example storing these measurements, and/or a date of the first use of each sensor to calculate an expiry date of the sensor(s) (the biochemical sensors have a limited lifespan). The data processing means are also used to generate instructions towards various components. In the framework of this description, these different functions are performed by the same unit. However, it is possible to provide for dedicated processors. The system also comprises a battery, advantageously a rechargeable battery, for the electrical supply to the components, for example via a port (understood as also being able to be used to connect the system 1, for example to a computer for downloading the acquired and/or processed data).

Preferably, the system 1 can comprise wireless connection means (particularly of the WiFi but also Bluetooth or even 3G/4G type) for a connection to a network, particularly the Internet, and a user interface such as a screen, possibly touch screen to display the monitoring results to the user.

Those skilled in the art are familiar with algorithms for processing sensor measurements 24 and the associated interfaces, and will know how to implement them in the present system 1.

The casing 120 further comprises electrical connectors, on its coupling face 122 with the coupling face 222 of the capsule 220.

The capsule 220 of the second module 200 has the shape of a closed, typically sealed, box which can be coupled with the casing 120. This capsule 220 is interchangeable, which allows obtaining an economical and efficient system, where only the parts said consumables need to be changed. The capsule 220 may have an annular shape, with a through opening 224 in the center. In a variant mentioned above, the sensor is positioned inside the capsule 220 (or in the casing 120) and analyzes the fluid sampled by the microneedles. The capsule 220 comprises electrical connectors 226, on a coupling face 222 with the casing 120, which can cooperate with the electrical connectors of the casing 120. If there is fluid transmission from the second to the first module, then complementary fluid connectors are provided on the capsule 220 and the casing 120.

Finally, the second module 200 comprises a patch 250, removably secured to the capsule 220, which is described in detail below.

The second module 200 (capsule 220 and patch 250) forms an interchangeable assembly of the system which is chosen according to the desired monitoring type and according to the state of deterioration of the microneedles 210 and/or of the sensor.

Indeed, insofar as the capsule 220 contains the microneedles 210 and/or the sensor (in particular in the case of microneedles that take a sample), changing the capsule 220 allows changing the equipment if it is at the end of its life or if it is desired to change the measured physical quantity, in a simple, fast and safe handling, without having to throw away other parts (particularly the first module 100).

Insofar as the capsule 220 minimizes the amount of expensive elements and/or materials (advanced electronic equipment such as a battery or wireless communication means), it is relatively inexpensive.

The invention claimed is:

1. A body monitoring system sensor, comprising analyte measurement microneedles configured to be inserted into the skin to sample and/or analyze a body fluid from the wearer of the sensor when the latter is positioned on the limb,
   wherein the analyte measurement microneedles extend parallel to a main direction from a substrate, define a working plane corresponding to the plane passing through the tip of the analyte measurement microneedles, the analyte measurement microneedles each comprising on their surface a biochemical material able to react with the analyte,
   wherein the sensor comprises at least one microneedle separate from the analyte measurement microneedles, on which is mounted a conductivity electrode configured to measure a level of penetration of the analyte measurement microneedles in the epidermis, the conductivity measurement electrode comprising a metal track, the end of the metal track extending along the main direction up to a position comprised strictly between the substrate and the working plane, the two being therefore excluded,
   the sensor comprising another conductivity electrode, operating as a reference conductivity electrode, said reference electrode comprising a metal track whose end can reach the working plane.

2. The sensor according to claim 1, wherein the metal track of each conductivity electrode has a length smaller than that of the analyte measurement microneedles.

3. The sensor according to claim 2, wherein the two tracks have the same length.

4. The sensor according to claim 1, wherein each conductivity electrode is mounted on a conductivity microneedle, of a length equal to that of the analyte measurement microneedles.

5. The sensor according to claim 1, wherein the conductivity electrode is mounted on a conductivity microneedle which is only partially coated with the metal track.

6. The sensor according to claim 1, comprising, distributed over one or several conductivity microneedle(s), a plurality of conductivity electrodes each comprising a metal track extending along the main direction up to at least two different positions, the positions being strictly comprised between the substrate and the working plane.

7. The sensor according to claim 6, wherein the metal tracks are all placed on the same microneedle.

8. The sensor according to claim 6, wherein the two positions are spaced by 200 to 400 µm along the main direction.

9. The sensor according to claim 6, wherein the end of the track of the reference conductivity electrode is at the same position as the end of the metal track of the longest conductivity electrode.

10. The sensor according to claim 7, wherein the microneedle has a frustoconical pyramidal shape comprising at least two faces and wherein the metal tracks are distributed over several faces.

11. The sensor according to claim 10, wherein the metal tracks are placed on different microneedles.

12. The sensor according to claim 10, wherein the metal tracks are distributed over several faces, one track per face.

13. The sensor according to claim 1, wherein the arrangement of the conductivity electrodes is made such that the analyte measurement microneedles are located between two conductivity microneedles.

14. A body monitoring system intended to be attached to a limb, comprising:
   a capsule comprising a sensor according to claim 1,
   a casing, able to be coupled with the capsule, inside which there is a battery and a processor, the processor being configured to process data obtained using the sample or the measurement taken by the microneedles, the processor and the battery being configured to manage the conductivity measurements using the electrodes.

15. The body monitoring system according to claim 14, comprising:
   a strap or a bracelet, configured to hold the casing in place on a limb, and a patch, the capsule being removably attachable to the patch and the patch being removably attachable to the casing, the patch having an adhesive role.

16. A method for measuring the level of penetration in the epidermis of the analyte measurement microneedles of a sensor according to claim 1, comprising at least one step of measuring the conductivity between a conductivity electrode and the reference conductivity electrode.

* * * * *